(12) United States Patent
Montañez-Soto

(10) Patent No.: US 10,232,004 B2
(45) Date of Patent: Mar. 19, 2019

(54) **PHARMACEUTICAL COMPOSITION BASED ON CENTELLA ASIATICA (*HYDROCOTYLE ASIATICA* L.) FOR THE TREATMENT OF LOWER LIMB ULCERS**

(71) Applicant: Flor Lucía Montañez-Soto, Veracruz (MX)

(72) Inventor: Flor Lucía Montañez-Soto, Veracruz (MX)

( * ) Notice: Subject to any disclaimer, the term of this patent is extended or adjusted under 35 U.S.C. 154(b) by 282 days.

(21) Appl. No.: 14/784,085

(22) PCT Filed: Apr. 9, 2014

(86) PCT No.: PCT/IB2014/000510
§ 371 (c)(1),
(2) Date: Oct. 13, 2015

(87) PCT Pub. No.: WO2014/167405
PCT Pub. Date: Oct. 16, 2014

(65) Prior Publication Data
US 2016/0074454 A1 Mar. 17, 2016

(30) Foreign Application Priority Data
Apr. 11, 2013 (MX) .................... MX/a/2013/004077

(51) Int. Cl.
| | | |
|---|---|---|
| *A61K 9/00* | (2006.01) | |
| *A61K 36/23* | (2006.01) | |
| *A61K 38/48* | (2006.01) | |
| *A61K 45/06* | (2006.01) | |
| *A61K 31/165* | (2006.01) | |
| *A61K 31/197* | (2006.01) | |
| *A61K 31/496* | (2006.01) | |
| *A61K 31/635* | (2006.01) | |
| *A61K 31/427* | (2006.01) | |

(52) U.S. Cl.
CPC ............ *A61K 36/23* (2013.01); *A61K 9/0014* (2013.01); *A61K 31/165* (2013.01); *A61K 31/197* (2013.01); *A61K 31/427* (2013.01); *A61K 31/496* (2013.01); *A61K 31/635* (2013.01); *A61K 38/4886* (2013.01); *A61K 45/06* (2013.01); *C12Y 304/24003* (2013.01)

(58) Field of Classification Search
None
See application file for complete search history.

(56) References Cited

U.S. PATENT DOCUMENTS

| | | |
|---|---|---|
| 4,318,906 A | 3/1982 | Llopart |
| 2004/0131706 A1 | 7/2004 | Rittinghausen et al. |
| 2007/0154425 A1 | 7/2007 | Potin |
| 2008/0014162 A1 | 1/2008 | Willemin et al. |
| 2009/0285868 A1 | 11/2009 | Richard et al. |
| 2010/0062085 A1 | 3/2010 | Widgerow |
| 2010/0086502 A1* | 4/2010 | Lucet-Levannier ..... A61K 8/35 424/60 |
| 2011/0151030 A1 | 6/2011 | Myhill et al. |

FOREIGN PATENT DOCUMENTS

| | | |
|---|---|---|
| EP | 1221325 A2 | 7/2002 |
| WO | 2012117340 A1 | 9/2012 |

OTHER PUBLICATIONS

Singh, S. et al. "Centella Asiatica: A plant with Immense Medicinal Potential But Threatened" International Journal of Pharmaceutical Sciences Review and Research, pp. 9-17, vol. 4. Issue 2. Sep.-Oct. 2010.
Babu, MK et al. "Comparison of the dermal wound healing of Centella Asiatica extract impregnated collagen and crosslinked collagen scaffolds" Journal of Chemical & Pharmaceutical Research, pp. 353-362, 2011.

* cited by examiner

*Primary Examiner* — Sharmila G Landau
*Assistant Examiner* — Stephen M Chong
(74) *Attorney, Agent, or Firm* — Browdy and Neimark, PLLC

(57) ABSTRACT

A pharmaceutical composition based on *centella asiatica* (*Hydrocotyle asiatica* L.) for the treatment of lower limb ulcers, including as active ingredients, *centella asiatica* and sodium acexamate in amounts producing a reciprocal synergistic effect when mixed with at least one adjuvant selected from a healing agent, an antibiotic agent and/or combinations thereof is described.

8 Claims, 26 Drawing Sheets

PHARMACEUTICAL COMPOSITION BASED ON CENTELLA ASIATICA (*HYDROCOTYLE ASIATICA* L.) FOR THE TREATMENT OF LOWER LIMB ULCERS

TECHNICAL FIELD

The present invention relates to the treatment of skin wounds and, more particularly, relates to a pharmaceutical composition based on *Hydrocotyle asiatica* L. for the treatment of lower limb ulcers.

BACKGROUND

For some time now, lower limb ulcers of diabetics have been a frequent reason for consultation to both the general practitioner and the specialist. Ulcers consist of the loss of epidermis and all or part of the dermis, also compromising the subcutaneous cellular tissue and muscle for several degrees of depth. These are formed because of a combination of factors occurring in the person such as lack of sensation in the foot, poor circulation, foot deformities, irritation (such as friction or pressure), and trauma. More particularly, those suffering from diabetes for a long time exhibit a high probability of developing neuropathy (damage to one or more nerves) on the lower limbs because of high levels of blood sugar, resulting in a reduction or lack of sensation in said area, which promotes the formation of ulcers.

Once a person has an ulcer, their quality of life is diminished as it is a painful wound that tends to easily become infected, despite appropriate care, as well as limiting their ability to move. This is a wound to which one should pay close attention because depending on its progress and severity, sometimes hospitalization of the affected person is necessary, and in more severe cases, amputation of an ulcer member, when it puts the patient's life at risk (the wound becomes a matter of life or death).

So far, the traditional management of this type of skin wounds is mainly based on the mechanical debridement of the affected area, topical application of substances and/or medicaments to promote healing, bandage over the affected area, and patient's rest. Among such used substances are antiseptics, antibiotics, topical vitamins, dextranomers, benzoyl peroxide, local vasodilators, etc., which do not provide the patient with reliable results and fast improvement.

There are natural remedies made from plant and roots extracts, which exhibit good qualities for skin regeneration and care. One of these remedies is obtained from the *Hydrocotyle asiatica* L. plant whose common name is *centella asiatica* or gotu kola, which is mainly composed by triperpenic compounds (asiatic acid, asiaticoside, madecassoside, and madecassic acid), tannins, oils, mucilages, pectins and phytosterols. Generally, the leaves of *centella asiatica* are used in infusions, but also its extract is used in the manufacture of creams and ointments.

In the prior art, several compositions to promote better healing of skin wounds such as ulcers or sores, which include *centella asiatica* extract as one of their main components can be found. Such is the case of European Patent Application No. EP 1 221 325A2, wherein a topical composition employing *centella asiatica* and *ginseng* extracts for skin wound healing as well as a process for the preparation thereof are described. Said composition comprises *centella asiatica* extract in 0.01-1% by weight and *ginseng* extract in 0.01-0.5% by weight as active agents. Likewise, depending on the formulating agents to be added to the composition, it may have a consistency of a gel or cream.

A drawback of the above described composition is that among its active and formulating agents, no antibiotic agent is found to prevent and fight infections of the skin wounds. Despite the curative qualities of ginseng, it would be desirable if such a composition included an active agent having a higher skin healing and regeneration activity.

Another example of compositions of this type is found in U.S. Patent Application No. US 2010/0062085A1, which describes a composition used to regenerate damaged skin tissue and, more specifically, it is used for the treatment of scars consequent upon surgeries. Said composition essentially comprises *Bulbine frutescens*, *centella asiatica* and one phenol extracted from olive oil (oleuropein). The percent of *centella asiatica* in the composition is from 0.45% to 0.55% mass/mass while the percent of *Bulbine frutescens* in the composition is from 9.9% to 11% mass/mass. The formulations obtained from this composition can be in the form of an ointment, cream, lotion, paste, gel, spray, or oil.

Although it is described that oleuropein has antiseptic properties (antifungal, antibiotic and anti-inflammatory), its spectrum is limited, so it would be advisable that said composition included a broad-spectrum antibiotic as an additional active agent.

Another example of compositions including *centella asiatica* is the composition described in U.S. Patent Application No. US 2004/0131706 A1, which is used for treating skin injuries caused by several factors such as viral diseases, fungi, allergic reactions etc., comprising natural or synthetic extracts from plants such as *Centella asiatica, Mahonia aquifolium, Viola tricolor*, among others. The weight percent in the composition of *Centella asiatica* is from 1 to 10%, of *Mahonia aquifolium* is from 1 to 10%, and of *Viola tricolor* is from 1 to 10%. Unlike other compositions of the prior art, said composition does not use zinc oxide.

As noted, the above described composition does not have an antibiotic among its active ingredients to prevent bacterial infections and promote a fast regeneration of new tissue.

OBJECTS OF THE INVENTION

Given the shortcomings of the prior art, an object of the present invention is to provide a pharmaceutical composition based on *Hydrocotyle asiatica* L. for the treatment of lower limb ulcers, which allows this type of wound to be cured quickly and efficiently.

Another object of the present invention is to provide a pharmaceutical composition based on *Hydrocotyle asiatica* L. for the treatment of lower limb ulcers, which allows the traditional treatment of this type of wounds to be improved.

It is another object of the present invention to provide a pharmaceutical composition based on *Hydrocotyle asiatica* L. for the treatment of lower limb ulcers that provides an antibacterial, antifungal, and skin tissue regeneration action.

A further object of the present invention is to provide a pharmaceutical composition based on *Hydrocotyle asiatica* L. for the treatment of lower limb ulcers, which, depending on the severity of the wound, eliminates pain on the first day of use, thus avoiding the intake of analgesics under treatment.

BRIEF DESCRIPTION OF THE DRAWINGS

The novel aspects that are regarded as characteristic of this invention will be particularly set forth in the accompanying claims. However, the invention itself, both by its structure and operation, together with further objects and advantages thereof, will be best understood from the following detailed description of a preferred embodiment when read in connection with the accompanying photos, in which:

Photo "1a" shows a venous ulcer wound on the left lower limb of a 72-year-old male patient, prior to undergoing the treatment with formulation I of the present invention. Treatment start date: Aug. 25, 2010.

Figure 1A:
Figure 1B:
Figure 2A:
Figure 2B:
Figure 3A:
Figure 3B:
Figure 4A:
Figure 4B:
Figure 5A:
Figure 5B:
Figure 6A:
Figure 6B:
Figure 7A:
Figure 7B:
Figure 8A:
Figure 8B:
Figure 9A:
Figure 9B:
Figure 10A:
Figure 10B:
Figure 11A:
Figure 11B:
Figure 12A:
Figure 12B:
Figure 13A:
Figure 13B:
Figure 14A:
Figure 14B:
Figure 15A:
Figure 15B:
Figure 16A:
Figure 16B:
Figure 17A:
Figure 17B:
Figure 18A:
Figure 18B:
Figure 19A:
Figure 19B:
Figure 20A:
Figure 20B:
Figure 21A:
Figure 21B:
Figure 22A:
Figure 22B:
Figure 23A:
Figure 23B:
Figure 24A:
Figure 24B:
Figure 25A:
Figure 25B:
Figure 26A:
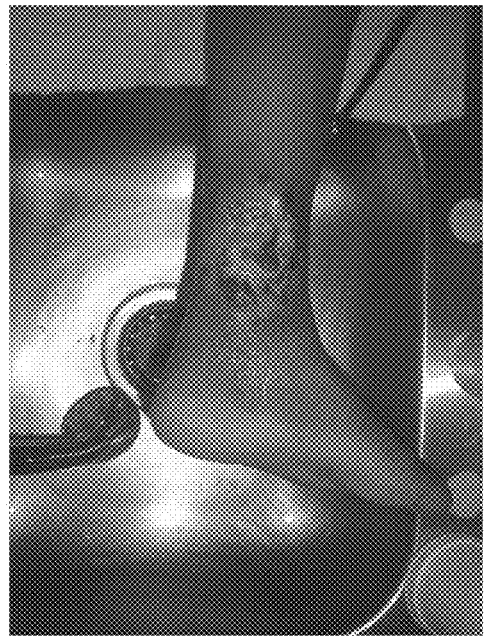
Figure 26B:

Photo "1b" shows the final result of healing of the wound as shown in photo "1a", once the treatment ended with formulation I of the present invention. Treatment end date: Sep. 1, 2010.

Photo "2a" shows a venous ulcer wound on the left lower limb of a 79-year-old male patient, prior to undergoing the treatment with formulation I of the present invention. Treatment start date: Nov. 17, 2011.

Photo "2b" shows the final result of healing of the wound as shown in photo "2a", once the treatment ended with formulation I of the present invention. Treatment end date: Dec. 21, 2011.

Photo "3a" shows a venous ulcer wound on the left lower limb of an 85-year-old male patient, prior to undergoing the treatment with formulation I of the present invention. Treatment start date: Mar. 2, 2009.

Photo "3b" shows the final result of healing of the wound as shown in photo "3a", once the treatment ended with formulation I of the present invention. Treatment end date: Dec. 16, 2009.

Photo "4a" shows a varicose ulcer wound on the left lower limb of a 58-year-old female patient, prior to undergoing the treatment with formulation I of the present invention. Treatment start date: Nov. 21, 2011.

Photo "4b" shows the final result of healing of the wound as shown in photo "4a", once the treatment ended with formulation I of the present invention. Treatment end date: Dec. 29, 2011.

Photo "5a" shows an ulcer wound on the right lower limb of a 64-year-old female patient, prior to undergoing the treatment with formulation I of the present invention. Treatment start date: Apr. 14, 2011.

Photo "5b" shows the final result of healing of the wound as shown in photo "5a", once the treatment ended with formulation I of the present invention. Treatment end date: Oct. 26, 2011.

Photo "6a" shows a varicose ulcer wound on the left lower limb of a 74-year-old female patient, prior to undergoing the treatment with formulation I of the present invention. Treatment start date: Nov. 10, 2010.

Photo "6b" shows the final result of healing of the wound as shown in photo "6a", once the treatment ended with formulation I of the present invention. Treatment end date: Jul. 26, 2011.

Photo "7a" shows a varicose ulcer wound on the right lower limb of a 73-year-old female patient, prior to undergoing the treatment with formulation I of the present invention. Treatment start date: Apr. 14, 2011.

Photo "7b" shows the final result of healing of the wound as shown in photo "7a", once the treatment ended with formulation I of the present invention. Treatment end date: Jul. 13, 2011.

Photo "8a" shows an ulcer wound on the right lower limb of a 55-year-old female patient, prior to undergoing the treatment with formulation I of the present invention. Treatment start date: May 24, 2010.

Photo "8b" shows the final result of healing of the wound as shown in photo "8a", once the treatment ended with formulation I of the present invention. Treatment end date: Jul. 15, 2010.

Photo "9a" shows a wound on the right diabetic foot of a 62-year-old male patient, prior to undergoing the treatment with formulation I of the present invention. Treatment start date: Aug. 3, 2011.

Photo "9b" shows the final result of healing of the wound as shown in photo "9a", once the treatment ended with formulation I of the present invention. Treatment end date: Nov. 3, 2011.

Photo "10a" shows a wound on the right diabetic foot of a 60-year-old male patient, prior to undergoing the treatment with formulation I of the present invention. Treatment start date: May 26, 2011.

Photo "10b" shows the final result of healing of the wound as shown in photo "10a", once the treatment ended with formulation I of the present invention. Treatment end date: Jul. 19, 2011.

Photo "11a" shows a wound on the left diabetic foot of a 67-year-old female patient, prior to undergoing the treatment with formulation I of the present invention. Treatment start date: Jan. 30, 2012.

Photo "11b" shows the final result of healing of the wound as shown in photo "11a", once the treatment ended with formulation I of the present invention. Treatment end date: Mar. 27, 2012.

Photo "12a" shows a highly complex wound on the right leg of a 32-year-old male patient, prior to undergoing the treatment with formulation II of the present invention. Treatment start date: Feb. 16, 2009.

Photo "12b" shows the final result of healing of the wound as shown in photo "12a", once the treatment ended with formulation II of the present invention. Treatment end date: Aug. 6, 2009.

Photo "13a" shows a trophic ulcer wound on the right foot of a 57-year-old female patient, prior to undergoing the treatment with formulation II of the present invention. Treatment start date: Oct. 29, 2007.

Photo "13b" shows the final result of healing of the wound as shown in photo "13a", once the treatment ended with formulation II of the present invention. Treatment end date: Jan. 31, 2008.

Photo "14a" shows a varicose ulcer wound on the left lower limb of a 58-year-old female patient, prior to undergoing the treatment with formulation II of the present invention. Treatment start date: May 16, 2011.

Photo "14b" shows the final result of healing of the wound as shown in photo "14a", once the treatment ended with formulation II of the present invention. Treatment end date: Jul. 11, 2011.

Photo "15a" shows a varicose ulcer wound on the right lower limb of a 60-year-old male patient, prior to undergoing the treatment with formulation II of the present invention. Treatment start date: May 20, 2010.

Photo "15b" shows the final result of healing of the wound as shown in photo "15a", once the treatment ended with formulation II of the present invention. Treatment end date: Dec. 27, 2010.

Photo "16a" shows an ulcer wound on the left lower limb of a 65-year-old female patient, prior to undergoing the treatment with formulation II of the present invention. Treatment start date: May 13, 2009.

Photo "16b" shows the final result of healing of the wound as shown in photo "16a", once the treatment ended with formulation II of the present invention. Treatment end date: Nov. 30, 2009.

Photo "17a" shows a highly complex wound on the left leg of an 82-year-old female patient, prior to undergoing the treatment with formulation II of the present invention. Treatment start date: Oct. 12, 2005.

Photo "17b" shows the final result of healing of the wound as shown in photo "17a", once the treatment ended with formulation II of the present invention. Treatment end date: Mar. 2, 2006.

Photo "18a" shows a varicose ulcer wound on the right lower limb of a 62-year-old female patient, prior to undergoing the treatment with formulation II of the present invention. Treatment start date: Jun. 18, 2007.

Photo "18b" shows the final result of healing of the wound as shown in photo "18a", once the treatment ended with formulation II of the present invention. Treatment end date: Jul. 16, 2008.

Photo "19a" shows a venous ulcer wound on the right lower limb of a 76-year-old female patient, prior to undergoing the treatment with formulation III of the present invention. Treatment start date: Oct. 5, 2011.

Photo "19b" shows the final result of healing of the wound as shown in photo "19a", once the treatment ended with formulation III of the present invention. Treatment end date: Feb. 8, 2012.

Photo "20a" shows an ulcer wound on the left lower limb of a 36-year-old female patient, prior to undergoing the treatment with formulation III of the present invention. Treatment start date: Oct. 20, 2011.

Photo "20b" shows the final result of healing of the wound as shown in photo "20a", once the treatment ended with formulation III of the present invention. Treatment end date: Feb. 1, 2012.

Photo "21a" shows an ulcer wound on the right lower limb of a 57-year-old female patient, prior to undergoing the treatment with formulation III of the present invention. Treatment start date: Jul. 22, 2010.

Photo "21 b" shows the final result of healing of the wound as shown in photo "21a", once the treatment ended with formulation III of the present invention. Treatment end date: Apr. 28, 2011.

Photo "22a" shows a venous ulcer wound on the right lower limb of a 77-year-old female patient, prior to undergoing the treatment with formulation III of the present invention. Treatment start date: Oct. 17, 2011.

Photo "22b" shows the final result of healing of the wound as shown in photo "22a", once the treatment ended with formulation III of the present invention. Treatment end date: Dec. 26, 2011.

Photo "23a" shows a wound on the left diabetic foot of a 54-year-old female patient, prior to undergoing the treatment with formulation III of the present invention. Treatment start date: Apr. 28, 2011.

Photo "23b" shows the final result of healing of the wound as shown in photo "23a", once the treatment ended with formulation III of the present invention. Treatment end date: Jun. 1, 2011.

Photo "24a" shows an ulcer wound on the left lower limb of a 67-year-old female patient, prior to undergoing the treatment with formulation III of the present invention. Treatment start date: Jun. 2, 2010.

Photo "24b" shows the final result of healing of the wound as shown in photo "24a", once the treatment ended with formulation III of the present invention. Treatment end date: Aug. 11, 2010.

Photo "25a" shows an ulcer wound on the right buttock of a 65-year-old female patient, prior to undergoing the treatment with formulation III of the present invention. Treatment start date: Aug. 25, 2011.

Photo "25b" shows the final result of healing of the wound as shown in photo "25a", once the treatment ended with formulation III of the present invention. Treatment end date: Feb. 28, 2010.

Photo "26a" shows a varicose ulcer wound on the right lower limb of a 57-year-old female patient, prior to undergoing the treatment with formulation III of the present invention. Treatment start date: Apr. 26, 2010.

Photo "26b" shows the final result of healing of the wound as shown in photo "26a", once the treatment ended with formulation III of the present invention. Treatment end date: Aug. 5, 2010.

BRIEF DESCRIPTION OF THE INVENTION

Compositions of the present invention are preferably used for the treatment of lower limb ulcers, and contain *centella asiatica* and sodium acexamate as active ingredients.

In a preferred embodiment of the present invention, the composition comprises from about 10% to 18% of *centella asiatica*; from about 67% to 75% of sodium acexamate; from about 10% to 18% of chloramphenicol; and about 60 U of collagenase (clostridiopeptidase A).

In a particularly preferred embodiment of the composition used in the present invention, said composition comprises about 14% of *centella asiatica*; about 71% of sodium acexamate; about 14% of chloramphenicol; and 60 U of collagenase (clostridiopeptidase A).

In another preferred embodiment of the present invention, the composition comprises from about 10% to 18% of *centella asiatica*; from about 67% to 75% of sodium acexamate; and from about 10% to 18% of sulfathiazole powder.

In a particularly preferred embodiment of the composition used in the present invention, said composition comprises about 14% of *centella asiatica*; about 71% of sodium acexamate; and about 14% of sulfathiazole powder.

In a further embodiment of the present invention, the composition comprises from about 10% to 18% of *centella asiatica*; from about 67% to 75% of sodium acexamate; and from about 10% to 18% of ciprofloxacin.

In a particularly preferred embodiment of the composition used in the present invention, said composition comprises about 14% of *centella asiatica*; about 71% of sodium acexamate; and about 14% of ciprofloxacin.

DETAILED DESCRIPTION OF THE INVENTION

The present invention relates to a pharmaceutical composition based on *centella asiatica* (*Hydrocotyle asiatica* L.), in combination with sodium acexamate for the treatment of lower limb ulcers.

In accordance with one of the aspects of the invention, a medicament in the form of an ointment, cream, gel or the like for topical application to the patient's skin for the treatment of lower limb ulcers, comprising *centella asiatica* (*Hydrocotyle asiatica* L.) and sodium acexamate, supplemented by one or more adjuvants is provided.

The treatment of ulcers essentially consists of a topical administration of a mixture of compounds comprising *centella asiatica* (*Hydrocotyle asiatica* L.) and sodium acexamate as active ingredients.

Among the supplements used as adjuvants to enhance the therapeutic effect of the mixture of the present invention are the following compounds: healing agents such as collagenase (clostridiopeptidase A); and antibiotic agents such as chloramphenicol, sulfathiazole, and ciprofloxacin or any other antibiotic agent as required, depending on the infection to be treated.

The compound commonly known as *centella asiatica* (*Hydrocotyle asiatica* L.), is a magnolophyta phanerogam plant of the genus *Centella* in the Apiaceae family, also known as Gotu Kola, Antanan, Pegaga, and Brahmi.

*Centella asiatica* as such has great properties in both cosmetic and therapeutic aspects. One of the first properties discovered for this plant, was its high and fast tissue healing and repairing power, which is an exceptional property for treating wounds, burns, skin sores, acne, etc.

Besides stimulating collagen formation, *centella asiatica* has healing and calming effects because of its nature. It is known that if the plant is placed as a poultice over wounds, it turns out to be a very effective remedy that helps healing.

Meanwhile, sodium acexamate, also known as 6-acetylaminocaproic acid, acexamic acid, 6-acetamidohexanoic acid, or 6-(acetylamino)hexanoic acid, has a Molecular Weight of 173.2096 g/mol and the Molecular Formula $C_8H_{15}NO_3$.

Sodium acexamate is a compound which mechanism of action is involved in the protein action of the collagen, enabling it to act in the healing process by regulating the production of fibroblasts and arrangement of collagenous fibers.

It shows poor absorption by cutaneous administration, remaining almost unchanged at the site of application, a property that is exploited to achieve a therapeutic effect at the site of injury. Also, by salifying it with sodium a higher absorption is obtained at a local tissue level.

Sodium acexamate also has an antiseptic effect that stimulates the fibroblast action to form fibers, thus contributing to the formation of the dermal matrix.

Meanwhile, collagenase is a zinc-containing enzyme that cleaves peptide bonds of type (I, II, III, IV, V) collagens. Collagenase belongs to a family of enzymes from various cellular sources and specificities for different substrates. Besides degrading collagen such as MMP (matrix metalloproteinase), these enzymes inactivate AAT (alpha-1-antitrypsin) and activate TNF-alpha (Tumor Necrosis Factor alpha).

Collagenase mainly acts on connective tissue in muscle cells and on some other parts of the body.

Medicinal collagenase (clostridiopeptidase A) is an enzyme that is extracted from a *clostridium* growth medium and is used to remove cellular and extracellular debris from necrotic tissue.

It has been approved as a medicament for use as a healing agent, so it is generally used in ulcers, bedsores, burns and injuries, as it helps in the formation of new tissue and re-epithelialization of skin ulcers and bedsores. Collagen of healthy or newly formed tissue was found not to be attacked by collagenase.

Chloramphenicol is a broad-spectrum antibiotic which was obtained for the first time from soil bacteria of the family of Actinomycetales, *Streptomyces venezuelae* and is currently produced by synthesis.

Chloramphenicol is thermally stable, effective against a wide range of microorganisms, particularly staphylococci, but due to its serious side effects (damage to the bone marrow, including aplastic anemia) in humans its use is limited to very serious infections such as typhoid fiber.

Sulfathiazole is a sulphonamide for external use, used as a healing and anti-infective agent which has the molecular formula $C_9H_9N_3O_2S_2$.

Sulfamides are poorly soluble in water so that when used in a powder form increase the residence time on wounds.

It is a white crystalline powder having antiseptic and healing action, which within its antiseptic action, antibacterial action is highlighted. It is used on wounds to prevent infections and promote healing, besides being used in other preparations as antiseptic active ingredient.

Ciprofloxacin is a broad-spectrum antibiotic of the fluoroquinolone group having bactericidal effects.

It is active against Gram-positive and Gram-negative bacteria. It works by inhibiting DNA gyrase, type II topoisomerasa, which is an enzyme needed to cleave replicated DNA, inhibiting cell division. It is effective against Enterobacteriaceae, *Vibrio, Haemophilus influenzae, Haemophilus ducreyi, Neisseria gonorrhoeae, Neisseria meningitidis, Moraxella catarrhalis, Brucella, Campylobacter, Mycobacterium intracellulare, Legionella* sp., *Pseudomonas aeruginosa, Bacillus anthracis*. In cell culture, it is used to treat *mycoplasma* infections.

The compounds *centella asiatica* and sodium acexamate which are employed for the manufacture of a medicament used in the treatment of lower limb ulcers, namely, diabetic foot and traumatic and/or surgical wounds of the lower limbs, are preferably applied in the form of mixtures in combination with adjuvants, particularly forming appropriate mixtures being employed for topical administration of medicaments.

Mixtures of the present invention may take a wide variety of forms, preferably taking the form of an ointment or salve.

The ointment of the present invention, used for the treatment of lower limb ulcers such as those present in the diabetic foot, comprises the *centella asiatica* and sodium acexamate active ingredients, and at least one adjuvant. The *centella asiatica* used is in the form of an ointment and powders, and sodium acexamate is found in the form of a cream and/or ointment.

Medicaments of the present invention, due to their activity spectrum, allow both the diabetic foot and varicose ulcer caused by Gram-positive bacteria, Gram-negative bacteria, and anaerobic bacteria to be treated.

In another aspect, the present invention relates to compositions comprising *centella asiatica* and sodium acexamate in amounts producing a reciprocal synergistic effect when mixed with at least one adjuvant selected from a healing agent, an antibiotic agent and/or combinations thereof.

Compositions of the present invention are preferably used for the treatment of lower limb ulcers, and contain *centella asiatica* and sodium acexamate as active ingredients.

In a preferred embodiment of the present invention, the composition comprises from about 10% to 18% of *centella asiatica*; from about 67% to 75% of sodium acexamate; from about 10% to 18% of chloramphenicol; and about 60 U (Units of Enzyme Activity) of collagenase (clostridiopeptidase A).

In a particularly preferred embodiment of the composition used in the present invention, said composition comprises about 14% of *centella asiatica*; about 71% of sodium acexamate; about 14% of chloramphenicol; and 60 U of collagenase (clostridiopeptidase A).

In another preferred embodiment of the present invention, the composition comprises from about 10% to 18% of *centella asiatica*; from about 67% to 75% of sodium acexamate; and from about 10% to 18% of sulfathiazole powder.

In a particularly preferred embodiment of the composition used in the present invention, said composition comprises about 14% of *centella asiatica*; about 71% of sodium acexamate; and about 14% of sulfathiazole powder.

In a further embodiment of the present invention, the composition comprises from about 10% to 18% of *centella asiatica*; from about 67% to 75% of sodium acexamate; and from about 10% to 18% of ciprofloxacin.

In a particularly preferred embodiment of the composition used in the present invention, said composition comprises about 14% of *centella asiatica*; about 71% of sodium acexamate; and about 14% of ciprofloxacin.

The ointment or salve for the treatment of lower limb ulcers can be prepared following methods generally employed in techniques for preparing pharmaceutical formulations having this presentation, namely, manual mixing by mortar, to finally obtain the ointment or salve through the obtained mixtures.

The following examples are intended to illustrate and not limit the scope of the present invention in all its aspects.

Composition Examples

Three pharmaceutical formulations in the form of an ointment are prepared, which contain:

Formulation I

| | |
|---|---|
| Standardized extract from dried leaves of *centella asiatica* | 1000 mg. |
| Sodium acexamate | 5000 mg. |
| Collagenase (clostridiopeptidase A) | 60 U. |
| Chloramphenicol | 1000 mg. |

Formulation II

| | |
|---|---|
| Standardized extract from dried leaves of *centella asiatica* | 1000 mg. |
| Sodium acexamate | 5000 mg. |
| Sulfathiazole powder | 1000 mg. |

Formulation III

| | |
|---|---|
| Standardized extract from dried leaves of *centella asiatica* | 1000 mg. |
| Sodium acexamate | 5000 mg. |
| Ciprofloxacin | 1000 mg. |

The ointment preparation includes the step of mixing each formulation with the active ingredient.

Pharmacological Examples

A prospective open study in 26 patients between the age of 32 and 85 years with clinical symptoms of lower limb ulcers of different severity degrees was performed.

Patients received a treatment that consists of applying an ointment prepared with each of the Formulations I, II or III, prior asepsis of the ulcer or wound, the formulation was applied as required for each particular case based on the medical diagnosis. The ulcer with applied ointment was covered with a dressing and then covered with a bandage. The treatment was repeated every 3, 5 or 7 days, depending on each particular case. After ending the treatment, all patients exhibited 100% healing, so that it is considered to be a complete cure.

No side effects from the administration of this treatment scheme in patients were observed.

Results

Formulation I

1).—A 72-year-old hypertensive male with venous ulcer on the left lower limb began the treatment on Aug. 25, 2010 and was discharged on Sep. 1, 2010.

2).—A 79-year-old male with venous ulcer on the left lower limb began the treatment on Nov. 17, 2011 and was discharged on Dec. 21, 2011.

3).—An 85-year-old hypertensive, diabetic male with venous ulcer on the left lower limb began the treatment on Mar. 2, 2009 and was discharged on Dec. 16, 2009.

4).—A 58-year-old hypertensive female with varicose ulcer on the left lower limb began the treatment on Nov. 21, 2011 and was discharged on Dec. 29, 2011.

5).—A 64-year-old hypertensive female with ulcer on right lower limb began the treatment on Apr. 14, 2011 and was discharged on Oct. 26, 2011.

6).—A 74-year-old female with varicose ulcer on the left lower limb began the treatment on Nov. 10, 2010 and was discharged on Jul. 26, 2011.

7).—A 73-year-old hypertensive, diabetic female with varicose ulcer on the right lower limb began the treatment on Apr. 14, 2011 and was discharged on Jul. 13, 2011.

8).—A 55-year-old hypertensive female with ulcer on the right lower limb began the treatment on May 24, 2010 and was discharged on Jul. 15, 2010.

9).—A 62-year-old diabetic male with a right diabetic foot began the treatment on Aug. 3, 2011 and was discharged on Nov. 3, 2011.

10).—A 60-year-old diabetic and hypertensive male with a right diabetic foot began the treatment on May 26, 2011 and was discharged on Jul. 19, 2011.

11).—A 67-year-old diabetic female with a left diabetic foot began the treatment on Jan. 30, 2012 and was discharged on Mar. 27, 2012.

Formulation II

1).—A 32-year-old diabetic male with a right foot complex began the treatment on Feb. 16, 2009 and was discharged on Aug. 6, 2009.

2).—A 57-year-old hypertensive, diabetic female with trophic ulcer on the right foot began the treatment on Oct. 29, 2007 and was discharged on Jan. 31, 2008.

3).—A 58-year-old female with varicose ulcer on the left lower limb began the treatment on May 16, 2011 and was discharged on Jul. 11, 2011.

4).—A 60-year-old male with varicose ulcer on the right lower limb began the treatment on May 20, 2010 and was discharged on Dec. 27, 2010.

5).—A 65-year-old female with ulcer on the left lower limb began the treatment on May 13, 2009 and was discharged on Nov. 30, 2009.

6).—An 82-year-old female with a left foot complex began the treatment on Oct. 12, 2005 and was discharged on Mar. 2, 2006.

7).—A 62-year-old diabetic female with varicose ulcer on the right lower limb began the treatment on Jun. 18, 2007 and was discharged on Jul. 16, 2008.

Formulation III

1).—A 76-year-old female with venous ulcer on the right lower limb began the treatment on Oct. 5, 2011 and was discharged on Feb. 8, 2012.

2).—A 36-year-old female with ulcer on the left lower limb began the treatment on Oct. 20, 2011 and was discharged on Feb. 1, 2012.

3).—A 57-year-old diabetic female with ulcer on the right lower limb began the treatment on Jul. 22, 2010 and was discharged on Apr. 28, 2011.

4).—A 74-year-old hypertensive female with venous ulcer on the right lower limb began the treatment on Oct. 17, 2011 and was discharged on Dec. 26, 2011.

5).—A 54-year-old diabetic female with diabetic foot began the treatment on Apr. 28, 2011 and was discharged on Jun. 1, 2011.

6).—A 67-year-old female with ulcer on the left lower limb began the treatment on Jun. 2, 2010 and was discharged on Aug. 11, 2010.

7).—A 65-year-old hypertensive female with ulcer on the right buttock began the treatment on Aug. 25, 2011 and was discharged on Feb. 28, 2012.

8).—A 57-year-old diabetic and hypertensive female with varicose ulcer on the left lower limb began the treatment on Apr. 26, 2010 and was discharged on Aug. 5, 2010.

As can be seen from the examples, upon ending the treatments all patients exhibited 100% healing so that it is considered to be a complete cure.

No side effects from the administration of this treatment scheme in patients were observed.

In accordance with the above description, it could be seen that a mixture of the standardized extract from dried leaves of *centella asiatica*, sodium acexamate, and an antibiotic agent such as chloramphenicol, sulfathiazole powder, ciprofloxacin or any other antibiotic agent, depending on the infection to be treated, surprisingly exhibits a highly effective synergistic effect for healing lower limb ulcers, ensuring a high possibility of therapeutic success.

Although certain embodiments of the invention have been illustrated and described, it should be noted that numerous modifications to them are possible. The present invention, therefore, should not be regarded as restricted, except as required by the prior art and the spirit of the accompanying claims.

The invention claimed is:

1. A pharmaceutical composition based on *centella asiatica* (*Hydrocotyle asiatica* L.) for the treatment of lower limb ulcers, comprising about 10% to 18% by weight of *centella asiatica*, about 67% to 75% by weight of sodium acexamate, and about 10% to 18% by weight of an antibiotic agent.

2. A pharmaceutical composition based on *centella asiatica* (*Hydrocotyle asiatica* L.) for the treatment of lower limb ulcers according to claim 1, further comprising about 60 U of collagenase.

3. A pharmaceutical composition based on *centella asiatica* (*Hydrocotyle asiatica* L.) for the treatment of lower limb ulcers according to claim 2, wherein the collagenase is clostridiopeptidase A.

4. A pharmaceutical composition based on *centella asiatica* (*Hydrocotyle asiatica* L.) for the treatment of lower limb ulcers according to claim 1, wherein the antibiotic agent is selected from chloramphenicol, sulfathiazole powder, and ciprofloxacin.

5. A pharmaceutical composition based on *centella asiatica* (*Hydrocotyle asiatica* L.) for the treatment of lower limb ulcers according to claim 2, wherein the composition comprises about 14% by weight of *centella asiatica*; about 71% by weight of sodium acexamate; about 14% by weight of chloramphenicol; and about 60 U of collagenase.

6. A pharmaceutical composition based on *centella asiatica* (*Hydrocotyle asiatica* L.) for the treatment of lower limb ulcers according to claim 1 wherein the composition comprises about 14% by weight of *centella asiatica*; about 71% by weight of sodium acexamate; and about 14% by weight of sulfathiazole powder.

7. A pharmaceutical composition based on *centella asiatica* (*Hydrocotyle asiatica* L.) for the treatment of lower limb ulcers according to claim 1 wherein the composition comprises about 14% by weight of *centella asiatica*; about 71% by weight of sodium acexamate; and about 14% by weight of ciprofloxacin.

8. A method for treatment of lower limb ulcers comprising administering to a subject in need a medicament comprising a pharmaceutical composition based on *centella asiatica* (*Hydrocotyle asiatica* L.) as claimed in claim 1.

* * * * *